United States Patent
Jeon et al.

(10) Patent No.: US 9,845,280 B2
(45) Date of Patent: Dec. 19, 2017

(54) METHOD OF PRODUCING ESTOLIDE HAVING HIGH STRUCTURAL STABILITY

(71) Applicants: SK INNOVATION CO., LTD., Seoul (KR); SK LUBRICANTS CO., LTD., Seoul (KR)

(72) Inventors: Hee Jung Jeon, Daejeon (KR); Jong su Lee, Gwangju (KR); Yong Woo Kim, Daejeon (KR)

(73) Assignees: SK INNOVATION CO., LTD., Seoul (KR); SK LUBRICANTS CO., LTD., Seoul (KR)

(*) Notice: Subject to any disclaimer, the term of this patent is extended or adjusted under 35 U.S.C. 154(b) by 89 days.

(21) Appl. No.: 14/884,247

(22) Filed: Oct. 15, 2015

(65) Prior Publication Data
US 2016/0107976 A1    Apr. 21, 2016

(30) Foreign Application Priority Data

Oct. 21, 2014   (KR) .................. 10-2014-0142874

(51) Int. Cl.
*C11C 3/00*   (2006.01)
*C07C 67/04*  (2006.01)
(Continued)

(52) U.S. Cl.
CPC ............ *C07C 67/04* (2013.01); *C07C 1/2078* (2013.01); *C07C 1/24* (2013.01); *C07C 29/149* (2013.01); *C07C 51/09* (2013.01); *C07C 51/36* (2013.01); *C07C 51/44* (2013.01); *C07C 53/126* (2013.01); *C07C 67/303* (2013.01); *C07C 69/24* (2013.01); *C10M 105/36* (2013.01); *C10M 177/00* (2013.01); *C11C 1/00* (2013.01); *C11C 1/005* (2013.01); *C11C 3/12* (2013.01); *C07C 2521/04* (2013.01); *C07C 2521/06* (2013.01); *C07C 2523/755* (2013.01); *C07C 2523/883* (2013.01)

(58) Field of Classification Search
CPC ......................................................... C11C 3/00
USPC ................................................. 508/459–505
See application file for complete search history.

(56) References Cited

U.S. PATENT DOCUMENTS 6,018,063 A * 1/2000 Isbell .................. C10M 101/04
                                                           508/460
6,316,649 B1 * 11/2001 Cermak .............. C10M 101/04
                                                           508/485
(Continued)

FOREIGN PATENT DOCUMENTS

| EP | 527224 | 2/1993 |
|---|---|---|
| WO | 92/15548 | 9/1992 |
| WO | 2011/037778 | 3/2011 |

OTHER PUBLICATIONS

Isbell, et al., "Industrial Crops and Products," 23(3): 256-263 (2006).

*Primary Examiner* — Ellen McAvoy
(74) *Attorney, Agent, or Firm* — Abelman, Frayne & Schwab

(57) ABSTRACT

Disclosed is a method of producing an estolide having high structural stability, including: a) preparing a fatty acid mixture from biomass-derived oil; b) separating the fatty acid mixture into a C16 fatty acid and a C18 fatty acid; c) converting the C18 fatty acid into a C18 or C17 linear internal olefin; and d) subjecting the C18 or C17 linear internal olefin and the C16 fatty acid to an estolide reaction, thus obtaining an estolide.

14 Claims, 2 Drawing Sheets

(51) Int. Cl.

| | |
|---|---|
| *C10M 105/36* | (2006.01) |
| *C07C 1/24* | (2006.01) |
| *C07C 29/149* | (2006.01) |
| *C07C 53/126* | (2006.01) |
| *C10M 177/00* | (2006.01) |
| *C11C 1/00* | (2006.01) |
| *C11C 3/12* | (2006.01) |
| *C07C 67/303* | (2006.01) |
| *C07C 69/24* | (2006.01) |
| *C07C 1/207* | (2006.01) |
| *C07C 51/09* | (2006.01) |
| *C07C 51/36* | (2006.01) |
| *C07C 51/44* | (2006.01) |

(56) References Cited

U.S. PATENT DOCUMENTS

| | | | |
|---|---|---|---|
| 8,287,754 B1 * | 10/2012 | Bredsguard | C09K 5/044 252/68 |
| 8,741,822 B2 * | 6/2014 | Narine | C10M 105/40 508/463 |
| 9,139,792 B2 * | 9/2015 | Bredsguard | C10M 105/36 |
| 9,365,790 B2 * | 6/2016 | Bredsguard | C10M 105/36 |
| 9,617,499 B2 * | 4/2017 | Jeon | C11C 3/003 |
| 9,637,701 B2 * | 5/2017 | Kim | C10M 129/72 |
| 9,688,936 B2 * | 6/2017 | Jeon | C10M 105/36 |
| 9,714,209 B2 * | 7/2017 | Kim | C07C 67/04 |
| 2012/0322897 A1 | 12/2012 | Bredsguard | |
| 2015/0232410 A1 * | 8/2015 | Bertin | C10M 169/042 508/505 |
| 2016/0009630 A1 * | 1/2016 | Kim | C07C 51/44 554/122 |
| 2016/0009631 A1 * | 1/2016 | Kim | C07C 67/04 508/497 |
| 2016/0097014 A1 * | 4/2016 | Jeon | C10M 105/36 508/496 |
| 2016/0108304 A1 * | 4/2016 | Jeon | C11C 3/00 507/138 |
| 2016/0108343 A1 * | 4/2016 | Jeon | C07C 69/67 554/122 |

* cited by examiner

METHOD OF PRODUCING ESTOLIDE HAVING HIGH STRUCTURAL STABILITY

CROSS-REFERENCE TO RELATED APPLICATION

This application claims the benefit of Korean Patent Application No. 10-2014-0142874, filed Oct. 21, 2014, entitled "A method of producing estolides having high structure stability", which is hereby incorporated by reference in its entirety into this application.

BACKGROUND OF THE INVENTION

1. Technical Field

The present invention relates to a novel method of producing estolides, in which the advantageous properties of existing estolides are retained and the shortcomings thereof are solved, and more particularly, to a method of producing estolides having high structural stability.

2. Description of the Related Art

Petroleum resources, which significantly contribute to the pollution of the global environment, are strictly regulated at refineries. Moreover, petroleum resources obtained by raising S, N, heavy metals, aromatics, etc. up to the earth's surface from deep underground are refined to thereby produce lubricants, but such lubricants have low biodegradability. When introduced to ecosystems, such lubricants have great influences on biological circulatory systems, and problems of ecological disturbance caused by chemicals may occur in the real world. Furthermore, direct crude oil spills, chemical spills, and silent oil spills may occur, causing problems for ecosystems.

Thus, efforts to replace petroleum resources with environmentally friendly alternatives are being made. A representative material thereof is biomass-derived oil.

Biomass-derived oil is a primary product obtained by squeezing fruits resulting from planting and cultivating trees. Since carbon from such biomass-derived oil comes from $CO_2$ in the atmosphere of the earth, unlike mineral oil derived from fossil carbon, there is no additional generation of $CO_2$ in the atmosphere of the earth, and the $CO_2$ concentration in the atmosphere may in fact decrease, thus contributing to total $CO_2$ reduction through environmental rehabilitation. Consequently, the use of biomass-derived oil positively affects environmental rehabilitation, and may contribute to total $CO_2$ reduction through environmental rehabilitation, thereby allowing for the additional use of fossil carbon.

Although diesel has been used as a drilling fluid, at present only 100% environmentally friendly chemicals are permitted to be utilized based on legal regulations due to awareness of the problem of such environmental issues. As for diesel, biomass-derived environmentally friendly diesel is regulated to be compulsorily used in amounts less than 10% in most of the world, and the proportion thereof is gradually increasing.

As for lubricating oil, legal regulations for the use of environmentally friendly lubricating oil have not yet been introduced. Although ester lube has been introduced as an environmentally friendly lubricating oil, it is a chemical and is thus about four times as expensive as crude oil-based lubricating oil, and the production amount thereof is limited, making it impossible to produce the amounts required by markets. However, there is already consensus that currently useful lubricating oil is an environmental pollutant. Lubricating oil resulting from crude oil is known to have biodegradability of 10 to 30% on the basis of CEC analysis, and 1 liter of lubricating oil prepared from crude oil is already regarded as an environmental pollutant that pollutes 1 million liters of water. However, as techniques for manufacturing biomass-derived lubricating oil have been recently devised, the use of environmentally friendly lubricating oil has come to the fore. For example, regulations governing the use of environmentally friendly oil at places adjacent to oceans, rivers and the like have been passed in December 2013 in the USA, and a bill (California senate bill 916) stipulating that 25% of gasoline and diesel engine oil be replaced with environmentally friendly lubricating oil by 2017 has been proposed in California. Although the bill in California failed to be established due to the high cost of manufacturing environmentally friendly lubricating oil, the fundamental purport thereof resonates with most people, and there is a continuous need for the use of environmentally friendly lubricating oil.

In order to manufacture environmentally friendly lubricating oil having high biodegradability and containing no toxic materials (S, N, aromatics, heavy metals), methods of using biomass may be readily taken into consideration. Since biomass is an environmentally friendly material having a very high biodegradability of about 70 to 100% and does not contain toxic materials such as S, N, aromatics and heavy metals, when lubricating oil is manufactured using biomass, environmentally friendly lubricating oil as described above may be expected to result. Also, petroleum resources are problematic because $CO_2$, which is a greenhouse gas, is added to the earth's circulatory system, whereas biomass is a hydrocarbon that is already present in the earth's circulatory system. Hence, the additional conversion of biomass into lubricating oil means that the hydrocarbons of biomass are simply converted into lubricating oil in terms of the earth's overall circulatory system, advantageously preventing the additional generation of $CO_2$ in the earth's circulatory system. The existing biomass industry has problems such as the generation of only small amounts of biomass and the requirement to collect biomass, but biomass commercialization markets are becoming very large, and thus crude palm oil (CPO), soy bean oil (SBO) and the like may be traded in amounts of at least 1 million tons on open markets in Singapore and Indonesia. Furthermore, byproducts such as free fatty acids may be purchased in amounts of hundreds of thousands of tons on open markets, and may then be made into products, thus eliminating problems regarding the amounts and collection of materials.

These days, estolide is receiving great attention as a biomass-derived environmentally friendly lubricating oil. If bill 916 of California had been actually established, estolide was intended to be used as an environmentally friendly lubricating oil. The term 'estolide' refers to any material in which unsaturated double bonds of hydrocarbons are cross-linked with a carboxyl functional group. Estolide, which is naturally present in castor- or Lesquerella-derived vegetable oil, was noted as being simply synthesized by Penoyer et al in 1954, and thus shows promise as a novel product.

The applicability of estolide as lubricating oil (Group V, Ester base oil) was initially recognized due to the structural properties thereof. For example, triglyceride-derived estolide, which was prepared in the beginning, exhibits a good pour point (PP 9 to −36° C.) but has poor oxidation stability (RPVOT 29 to 52 min), and thus cannot be directly used as lubricating oil. As techniques have been devised for improving oxidation stability using oleic acid as an estolide feed through partial hydrogenation by use of an additive, the applicability thereof to high-quality lubricating base oil and cosmetic materials is significantly increasing.

A conventional process for producing estolide includes four steps of de-esterification, estolide synthesis, esterification, and hydrogenation. De-esterification is a step of converting triglycerides, which constitute most biomass-derived oil, into fatty acids, estolide synthesis is a step of converting unsaturated fatty acids into estolides, esterification is a step of converting the carboxyl functional group of an estolide into ester through a reaction with alcohol so as to stabilize it, and hydrogenation is a step of eliminating unsaturated double bonds from an estolide to thereby increase oxidation stability.

The estolide thus produced manifests characteristics of high-quality lubricating base oil having high viscosity index, oxidation stability and thermal stability, compared to conventional petroleum-based Group I, Group II, and Group III base oil products. Estolides are considerably favorable in terms of making lubricating base oil having high viscosity based on 100 vis.

However, conventional methods of producing estolides have the following problems.

The first problem is the dependence on oleic acid. Early estolide research was ongoing into the direct preparation of estolides from triglycerides so as to be used as lubricating base oil. However, in the case where a triglyceride is directly used, low-temperature stability may become problematic, and thus the resulting oil is unsuitable for use as lubricating base oil. Hence, as oleic acid is selectively used to produce estolide, the problem of low-temperature stability may be significantly alleviated, and the properties may be enhanced. In other words, the dependence on oleic acid is remarkably increased when producing estolide. However, the amount of biomass-derived oleic acid is limited. Table 1 below shows the hydrocarbon chains that constitute the triglycerides of CPO and SBO, which are commercially applicable. As is apparent form Table 1, oleic acid comprises about 52 wt % of palm oil. The remaining materials other than oleic acid are not contained in estolides, and are thus not used. Only the amount of biomass-derived oil corresponding to oleic acid may be used, which is merely 50 wt % at most. The remaining fatty acids other than oleic acid are disadvantageous in that there is no end use therefor.

TABLE 1

| Fatty acid | SBO | PO |
|---|---|---|
| 12:0 Lauric acid | | <1.2 |
| 14:0 Myristic acid | 0.4 | 0.5 to 5.9 |
| 14:1 Myristoleic acid | | |
| 16:0 Palmitic acid | 7 to 14 | 32 to 59 |
| 16:1 Palmitoleic acid | <0.5 | <0.6 |
| 18:0 Stearic acid | 1.4 to 5.5 | 1.5 to 8.0 |
| 18:1 Oleic acid | 19 to 30 | 27 to 52 |
| 18:2 Linoleic acid | 44 to 62 | 5.0 to 14 |
| 18:3 Linolenic acid | 4.0 to 11 | <1.5 |
| 20:0 Eicosanoic acid | <1.0 | <1.0 |
| 22:0 Docosanoic acid | <1.0 | |

Second, alcohol is essentially required for esterification. Due to the presence of the fatty acid functional group, a variety of problems related to material stability and corrosion may occur in the estolide reaction, and thus such a functional group has to be converted into some other stable form. Typically, it is converted into ester, which has high stability and from which a volume gain may be expected. In order to convert estolide into ester, an acid functional group is conventionally reacted with alcohol, and is thus stabilized in the form of ester. In other words, alcohol is necessarily required in order to achieve reaction stabilization. Since alcohol is not produced during the reaction, it has to be introduced from the outside.

Third, hydrotreating is essentially required. In conventional estolide production reactions, hydrofinishing is performed in order to remove unsaturated double bonds from biomass-derived oil. Since oxidation stability is decreased in the presence of unsaturated double bonds, such unsaturated double bonds must be essentially removed through hydrogenation. In the conventional estolide reaction, unsaturated double bonds of estolides are eliminated through hydrogenation, especially hydrofinishing. However, hydrogenation is problematic because it requires reaction conditions of high temperature and high pressure and also because the price of hydrogen is very high, undesirably negating economic benefits. Hence, the production of estolides without conducting hydrogenation is regarded as very desirable.

Fourth, there may remain unsaturated double bonds in estolides, despite the reaction for removing unsaturated double bonds using such hydrogenation. In the case where lubricating oil has unsaturated double bonds in the molecular structure thereof, there may occur side reactions, including discoloration through the coupling of unsaturated double bonds and oxygen in air, and the high likelihood of corrosion due to high bindability with moisture in the air. Accordingly, it is important that unsaturated double bonds are completely removed through hydrogenation so that no unsaturated double bonds remain. For estolides, some ester bonds may break in the course of the reaction for completely removing unsaturated double bonds, and thus selective removal of unsaturated double bonds is carried out under the condition that ester bonding is maintained. For this reason, it is difficult to completely remove unsaturated double bonds. Unsaturated double bonds may be left behind at a level of less than 10 based on the iodine value.

Fifth, existing estolide has an ester functional group having low steric hindrance. Esterification is advantageous because the unique structural stability of ester may be expected, and also a volume gain due to alcohol may be expected. Although the ester functional group merely has relatively high stability compared to other functional groups, it is not absolutely stable. Depending on the reaction conditions, the ester functional group may be irreversibly converted into fatty acid. In this case, there may occur temporary but serious problems of aggravating the corrosion of engines. As for fatty acid methyl ester (FAME), which is a first-generation ester-type biodiesel, or for ester base oil, which is a Group V base oil, problems of the corrosion of engines attributable to fatty acids resulting from breaking the ester functional group are still reported. With the goal of overcoming such problems, another type of diesel or anti-corrosion additive may be used together therewith.

SUMMARY OF THE INVENTION

Accordingly, the present invention has been made keeping in mind the problems encountered in the related art, and an aspect of the present invention is to provide a novel method of producing estolides having high structural stability from biomass-derived oil that is present in nature.

In addition, an aspect of the present invention is to provide a method of producing estolides, which, among the kinds of biomass-derived fatty acids, adopts remaining fatty acid other than oleic acid, thus generating economic benefits.

In addition, an aspect of the present invention is to provide a method of producing estolides, which obviates the need for alcohol.

In addition, an aspect of the present invention is to provide an estolide having no unsaturated bonds.

In addition, an aspect of the present invention is to provide an estolide having high structural stability and a lubricating oil including the same.

An embodiment of the present invention provides a method of producing an estolide having high structural stability, comprising: a) preparing a fatty acid mixture from biomass-derived oil; b) separating the fatty acid mixture into a C16 fatty acid and a C18 fatty acid; c) converting the C18 fatty acid into a C18 or C17 linear internal olefin; and d) subjecting the C18 or C17 linear internal olefin and the C16 fatty acid to an estolide reaction, thus obtaining an estolide.

As such, c) may comprise converting the C18 fatty acid into a C18 linear internal olefin through partial hydrogenation and dehydration, and c) may comprise converting the C18 fatty acid into a C17 linear internal olefin through decarbonylation.

In an embodiment of the present invention, the method may further comprise e) performing hydrotreating to increase stearic acid content, after a).

In an embodiment of the present invention, the method may further comprise f) hydrotreating the C18 fatty acid separated in b) to increase stearic acid content.

In an embodiment of the present invention, a) or A) may be performed through de-esterification or hydrolysis of triglyceride in the biomass-derived oil.

Another embodiment of the present invention provides a method of producing an estolide having high structural stability, comprising: A) preparing a fatty acid mixture from biomass-derived oil; and B) subjecting the fatty acid mixture to an estolide reaction and then hydrodeoxygenation, thus obtaining an estolide.

In an embodiment of the present invention, the method may further comprise C) performing hydrotreating to increase stearic acid content, after A).

In an embodiment of the present invention, the method may further comprise D) separating or purifying the estolide obtained in B) to obtain a desired estolide.

In an embodiment of the present invention, A) may be performed through de-esterification or hydrolysis of triglyceride in the biomass-derived oil.

Still another embodiment of the present invention provides an estolide produced by the method as above.

Yet another embodiment of the present invention provides a lubricating oil comprising an estolide produced by the method as above.

In an embodiment of the present invention, the estolide may comprise an estolide represented by Chemical Formula 1 or Chemical Formula 2 below:

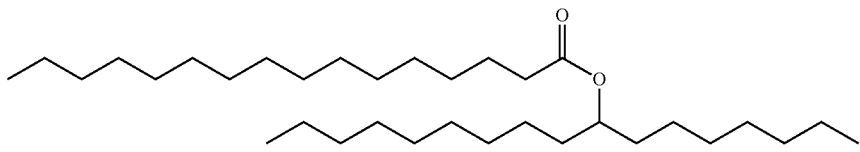

[Chemical Formula 1]

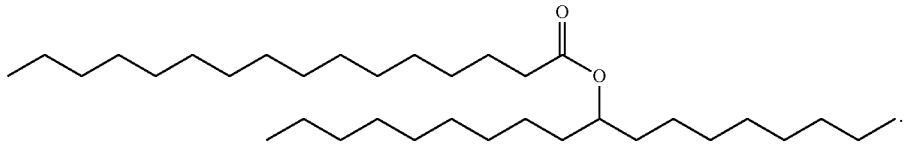

[Chemical Formula 2]

According to an embodiment of the present invention, an estolide product has no unsaturated double bonds, unlike existing products, and also contains an ester functional group having high steric hindrance, and additionally makes it possible to use any type of biomass-derived oil, unlike the conventional production of estolide, which uses only oleic acid.

According to an embodiment of the present invention, the conventional production of estolide is performed only using oleic acid, and thus the processing of remaining fatty acids other than oleic acid is required, but the production of the estolide of the invention has no remaining fatty acid byproducts, thus obviating the need for additional processing. Furthermore, hydrofinishing is not separately required, and final estolide products do not contain residual unsaturated double bonds. Moreover, since estolide has an ester functional group having high steric hindrance in the molecule thereof, conventional esterification is not additionally required, and it is difficult to convert the ester into acid, thereby exhibiting high structural stability.

Although only oleic acid is used in conventional estolide processes, fatty acids other than oleic acid can be utilized in the present invention, whereby no fatty acid byproduct remains, thus obviating the need for additional processing.

Also, the produced estolide can realize the advantages of environmentally friendly lubricating oil. For example, estolides can retain all advantages of lubricating oil, including high biodegradability, a high viscosity index, low-temperature stability, etc.

DESCRIPTION OF SPECIFIC EMBODIMENTS

Hereinafter, a detailed description will be given of embodiments of the present invention. Such embodiments are merely illustrative, but are not to be construed as limiting the present invention.

In an embodiment of the present invention, a method of producing estolide having high structural stability comprises a) preparing a fatty acid mixture from biomass-derived oil; b) separating the fatty acid mixture into C16 and C18 fatty acids; c) converting the C18 fatty acid into C18 or C17 linear internal olefin; and d) subjecting the C18 or C17 linear internal olefin and the C16 fatty acid to an estolide reaction, thus obtaining an estolide.

Figure 1:
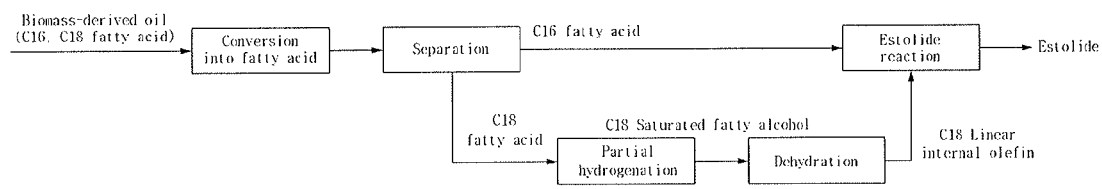
FIG. 1 schematically illustrates a production process according to an embodiment of the present invention.

In an exemplary embodiment referring to FIG. 1, the method of producing an estolide having high structural stability includes converting biomass-derived oil into a fatty acid mixture comprising C16 and C18 fatty acids. Then, the fatty acid mixture is separated into C16 fatty acid and C18 fatty acid, the separated C18 fatty acid is converted into C18 saturated fatty alcohol through partial hydrogenation, and the C18 saturated fatty alcohol is converted into C18 linear internal olefin through dehydration. Then, the C18 linear internal olefin and the separated C16 fatty acid are subjected to an estolide reaction, yielding an estolide.

Figure 2:
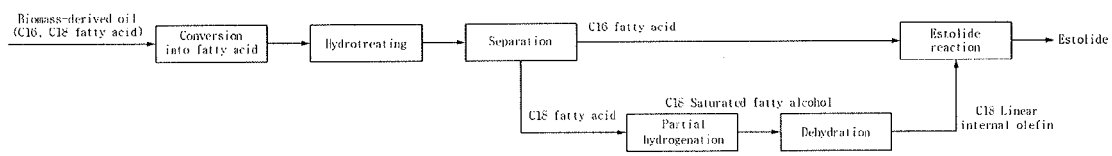
FIG. 2 schematically illustrates a production process according to another embodiment of the present invention.

In an exemplary embodiment referring to FIG. 2, hydrotreating the fatty acid mixture may be further performed, unlike the embodiment of FIG. 1.

Conversion of Biomass-Derived Oil Into Fatty Acid

A biomass-derived oil component mainly contains triglycerides and fatty acids. Triglycerides are present in the form of three fatty acids that are ester-linked to glycerol. As such, the ratio (by weight) of triglyceride to fatty acid in the biomass-derived oil is, for example, about 100:1 to 6:1, particularly about 20:1 to 6:1, and more particularly about 10:1 to 6:1, and may vary depending on the source of biomass and is not necessarily limited to the above numerical ranges. More typically, triglyceride may constitute about 90 to 95 wt % of biomass-derived oil.

Also, the carbon chain of triglyceride is approximately composed of C4 to C24, and more typically of C16 and C18. Such triglycerides, or some mono- and di-glycerides, may be converted into mixed C16 and C18 fatty acids through de-esterification, as represented by Scheme 1 below.

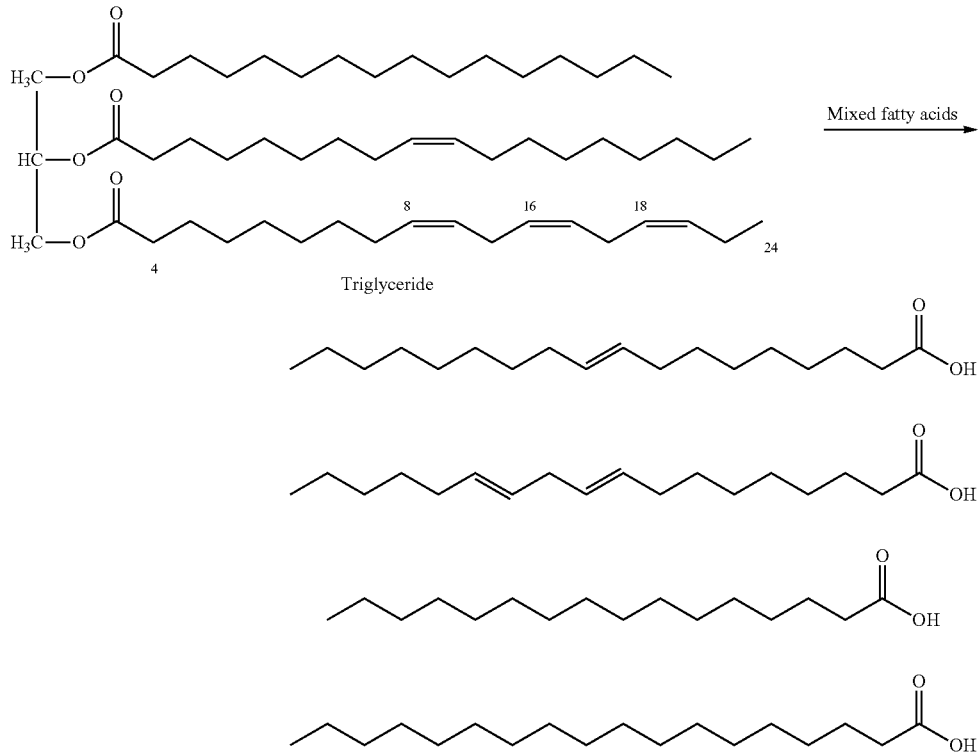

[Scheme 1]

De-esterification, illustrated as above, is a typical reaction for preparing fatty acid methyl ester (FAME) from biomass.

In an exemplary embodiment, de-esterification enables the conversion of triglyceride into fatty acid in the presence of a strong acid (e.g. $H_2SO_4$, $HNO_3$, HCl, HBr, HI, $HClO_4$, $HClO_3$, $HBrO_4$, $HBrO_3$, $HIO_4$, $HIO_3$, etc.) or a strong base (e.g. NaOH, KOH, $Ca(OH)_2$, an amine compound, etc.) or steam at high temperature (typically about 100 to 300° C., and more typically about 100 to 200° C.).

Also, ester bonds of triglycerides may be hydrolyzed, thus affording fatty acids. In addition, various reactions for converting triglycerides into fatty acids as known in the art may be adopted without particular limitation.

Separation of C16 and C18 Fatty Acids

The biomass-derived oil contains various kinds of saturated fatty acids and unsaturated fatty acids. Examples of fatty acids derived from palm oil may include myristic acid, palmitic acid, oleic acid, linoleic acid, linolenic acid, monoglyceride, and diglyceride. Various kinds of fatty acids have different boiling points, whereby desired fatty acids may be selectively extracted and separated through fractional distillation.

Thus, the converted biomass-derived fatty acids may be separated and extracted into C16 fatty acid and C18 fatty acid through fractional distillation. The C16 fatty acid may be palmitic acid, and the C18 fatty acid may include stearic acid, oleic acid, linoleic acid, linolenic acid, or a combination thereof.

Hydrotreating

In an embodiment of the present invention, hydrotreating may be further performed after a) or b), whereby stearic acid content may be increased.

Specifically, this process is related to converting C18:2 (linoleic acid), C18:3 (linolenic acid), or C18:1 (oleic acid), of the biomass-derived oil, into C18:0 (stearic acid).

When using hydrotreating at high temperature under high pressure, unsaturated double bonds may be completely converted into C18:0 (stearic acid).

For example, a catalyst for use in a hydrotreating reaction may be configured such that NiMo, CoMo, or Mo metal is loaded on a water-resistant carrier. The reaction may be carried out under conditions of about 250 to 300° C. and about 20 to 30 bar.

Under typical hydrogenation conditions of 300° C. or higher and hydrogen pressure of 40 bar or more, a carboxyl functional group is removed. Hence, hydrotreating according to the present process for selectively removing only unsaturated double bonds may be carried out under mild operating conditions. More specifically, under conditions of about 250 to 300° C. and about 20 to 30 bar using a NiMo/$ZrO_2$ catalyst, the C18 fatty acid having unsaturated double bonds may be converted into stearic acid.

As such, the catalyst and reaction conditions for hydrotreating are not limited thereto, and any hydrotreating conditions known in the art may be utilized so long as the C18 unsaturated fatty acid of the biomass-derived oil may be converted into the C18 saturated fatty acid.

The hydrotreating process according to the present invention is different from a conventional hydrotreating process in terms of the peculiarities of biomass itself. Biomass has very high oxygen content compared to crude oil. When oxygen is removed through the hydrotreating reaction, such oxygen may be removed in the form of $H_2O$ by the reaction with hydrogen, thus melting the active metal and the carrier of the catalyst, undesirably seriously causing the inactivation of the catalyst. Hence, hydrotreating of biomass may be seriously problematic because the catalyst may be inactivated due to the water byproduct. In the present technique, a water-resistant carrier such as $ZrO_2$, $TiO_2$, etc. is used, thereby overcoming the problem of inactivation of the catalyst owing to catalyst leaching.

Even when some of the unsaturated double bonds of the olefins may remain under the above reaction conditions, all fatty acids having unsaturated double bonds are converted into saturated fatty acids through recycling treatment. Therefore, the suppression of side reactions is regarded as more important than the reaction yield.

Conversion into C18 or C17 Linear Internal Olefin

The conversion of the separated C18 fatty acid into C18 or C17 linear internal olefin is described below.

The reactions for conversion into linear internal olefin may be largely classified into two types.

One type of reaction is carried out in a way such that fatty acid is converted into alcohol through hydrogenation, and then into linear internal olefin through dehydration. As such, since 2 mol of $H_2$ are fed per 1 mol of fatty acid to remove 2 mol of $H_2O$ to thereby prepare 1 mol of linear internal olefin, there is no weight reduction, and all of the processes used are fixed-bed processes, making it possible to achieve mass production. The reaction for producing fatty alcohol may operate using a Cu-based partial hydrogenation catalyst under conditions of about 200 to 400° C., $H_2$ pressure of about 20 to 100 bar, WHSV of about 0.05 to 10 $h^{-1}$, and a gas oil ratio (GOR) of about 50 to 5000, so that fatty acid is converted into fatty alcohol. Using a typical metal oxide catalyst for dehydration, the reaction is carried out under conditions of about 200 to 500° C., $N_2$ pressure of about 1 to 30 bar, WHSV of about 0.05 to 10 $h^{-1}$, and GOR of about 50 to 5000, yielding linear internal olefin.

The other type of reaction for preparing linear internal olefin is to use decarbonylation. Decarbonylation is carried out in a way such that two fatty acid molecules are converted into a fatty acid anhydride and one molecule of each of CO and $H_2O$ is removed, thereby yielding one molecule of linear internal olefin and one molecule of fatty acid. Mainly using a Fe-triphenyl phosphine chelate catalyst, linear internal olefin is prepared under conditions of 120 to 300° C. and $N_2$ or CO pressure of 1 to 70 bar in a batch reactor. In order to increase the decarbonylation activity, when a salt such as NaCl, KCl, NaI, or KI is added, the halogen material participates as the chelating agent of the catalyst, thereby accelerating the conversion into linear internal olefin. In order to remove water produced during the reaction and to accelerate the decarbonylation reaction rate, light acid is added in the form of an anhydride. Since the produced linear internal olefin is a material produced via decarbonylation, it has a number of carbons lower by 1 than the original number of carbons. This reaction has no large initial investment cost because the yield of linear internal olefin is high and a batch reactor is used.

When using the above two exemplary methods, linear internal olefin may be prepared, and the conversion into linear internal olefin is not necessarily limited thereto. Also, the type of preparation of linear internal olefin may be adopted depending on the need and industrial scale.

Production Reaction of Estolide

Estolide is synthesized through the estolide reaction between the C16 fatty acid and the C18 or C17 linear internal olefin.

A typical reaction for producing estolide is carried out using an acid catalyst. The acid for use in the catalyst is mainly a strong acid, such as $H_2SO_4$ or $HClO_4$, and an acid having intermediate strength such as formic acid may be used, but more severe conditions are required. The estolide reaction does not occur as rapidly as typical oligomerization and alkylation, thus causing no side reactions, and taking a long period of time under the estolide reaction conditions, thereby increasing the estolide yield. The experimental parameters for producing estolide include not only acidity, acid value, and temperature, but also reaction time and stirring rate. Although estolide is produced within several hours, the yield thereof is not high, and thus the reaction time is typically set to 12 hours or more. Furthermore, the stirring rate is regarded as very important. As the stirring rate is increased, the reaction may become more efficient. The reaction pressure is also important. Thus, the production of estolide at low reaction pressure is adopted because changes in color of the product may decrease and the yield may increase, but a vacuum unit is required.

A conventional method of producing estolide includes adding an acid catalyst to oleic acid and preparing estolide, which is then subjected to esterification with alcohol such as methanol without additional cutting, yielding a final estolide product. Accordingly, not only oleic acid dimer type estolides but also trimer or higher estolides may be produced simultaneously, and thus the product may be provided in the form of a mixture. Furthermore, since the ratio thereof is difficult to adjust, the produced materials have to be separately used, or the conditions for preparing reproducible mixtures have to be ensured.

The estolide reaction is typically carried out at a reaction temperature of 45 to 300° C. When a vacuum is applied, the estolide reaction is induced in the temperature range of −20 to 30° C. depending on the strength of the vacuum. Furthermore, the reaction can be induced using 0.01 to 20 wt % of an acid catalyst relative to the feed. The reaction for producing estolide is conducted under conditions of a reaction time of 0.5 to 48 hr, and a stirring rate of 50 to 2000 rpm.

Figure 3:
FIG. 3 schematically illustrates a production process according to still another embodiment of the present invention.

With reference to FIG. 3, biomass-derived oil is converted into a fatty acid mixture. Then, the fatty acid mixture is sequentially subjected to estolide reaction and hydrodeoxygenation, thus obtaining an estolide. As necessary, separating or purifying the estolide to isolate a desired estolide may be further performed.

The preparation of the fatty acid mixture from the biomass-derived oil is as described above. The fatty acid mixture may be a mixture of C16 fatty acid and C18 fatty acid, and may be subjected to an estolide reaction. To this end, the aforementioned estolide reaction may be applied. Below is a description of hydrodeoxygenation.

Hydrodeoxygenation

The catalyst for use in hydrodeoxygenation is configured such that NiMo, CoMo, or Mo metal is loaded on a water-resistant carrier. The reaction may be carried out under conditions of about 150 to 300° C. and $H_2$ pressure of about 10 to 30 bar, particularly about 170 to 250° C. and $H_2$ pressure of about 15 to 25 bar, and more particularly about 180° C. and $H_2$ pressure of about 20 bar, rather than typical hydrogenation conditions of high temperature of 250° C. or more and high pressure of 40 bar or more.

Upon hydrodeoxygenation, the reaction conditions are appropriately controlled, so that an ester functional group is left behind, and only a carboxyl functional group, which is externally exposed, is selectively removed. Such a selective reaction may be carried out by controlling the reaction conditions. When the reaction temperature is 350° C. or higher, ester is broken and is thus converted into linear paraffin. Hence, the reaction is conducted at about 200 to 250° C., at which carboxylic acid begins to be removed, and unreacted carboxylic acid may be recycled, thereby removing all carboxylic acids.

A better understanding of the present invention may be obtained via the following examples which are set forth to illustrate, but are not to be construed as limiting the present invention.

EXAMPLE 1

1512 g of palm fatty acid distillate (PFAD) as a byproduct of biomass-derived oil was cut at a boiling point of 360° C., thus obtaining 807 g of C18 unsaturated fatty acid. Through analysis of SimDist and GC-MS thereof, the ratios of C18:0, C18:1, C18:2, and C18:3 were measured. The results are shown in Table 2 below. The obtained PFAD-derived C18 unsaturated fatty acid was subjected to partial hydrogenation using a NiMo/$ZrO_2$ catalyst, and was thereby converted into C18 saturated fatty acid. The NiMo/$ZrO_2$ catalyst was prepared as follows.

Specifically, the catalyst was prepared by loading about 10 wt % of Mo and about 3 wt % of Ni on a $ZrO_2$ carrier having a diameter of 1 mm. The Mo precursor was ammonium heptamolybdate tetrahydrate (AHM), and the Ni precursor was nickel nitrate hexahydrate (NNH). Mo and Ni were fed using various precursors, but the invention is not limited thereto.

Specifically, an aqueous solution of AHM dissolved in deionized (DI) water was incorporated in a $ZrO_2$ carrier, dried at 150° C. for 2 hr, and continuously burned at 500° C. for 2 hr, thus obtaining Mo/$ZrO_2$.

Then, NNH was dissolved in DI water, impregnated with the Mo/$ZrO_2$ catalyst, dried at 150° C. for 2 hr, and continuously burned at 500° C. for 2 hr, yielding the NiMo/$ZrO_2$ catalyst.

6 cc of the catalyst thus prepared was placed in a cylindrical reactor, loaded with an R-LGO feed at a rate of 0.08 cc/min at room temperature, heated to 320° C. under conditions of a reaction pressure of 45 bar and $H_2$ flow rate of 16 cc/min, and pretreated for 3 hr at 320° C.

6 g of the NiMo/ZrO☐ catalyst thus pretreated was placed in a fixed-bed reactor, after which 807 g of the PFAD-derived C18 feed and 8.1 g of dimethyl disulfide (DMDS) were reacted at a rate of 0.1 cc/min (LHSV=1) under conditions of a reaction temperature of 240° C., a reaction pressure of 20 bar, and $H_2$ flow rate of 100 cc/min. The feed bottle was maintained at 70° C., and the reaction mixture was stirred and retained in a liquid phase. Sampling was conducted at 8-hr intervals, and the properties of the obtained products were measured through GC-MS, and the leaching of the catalyst was checked using ICP.

Based on the results of analysis of GC-MS, almost all of the unsaturated fatty acids were able to be converted into saturated fatty acids. Although C18:1 (oleic acid) was left behind in an amount of about 25%, it was able to be converted into C18:0 (stearic acid) through recycling treatment.

TABLE 2

| A series | A, Feed A | A, 240-20 |
|---|---|---|
| Myristic acid (14:0) | 0.0 | 0.0 |
| Palmitic acid (16:0) | 0.0 | 0.6 |
| Stearic acid (18:0) | 6.8 | 74.6 |
| Oleic acid (18:1) | 78.8 | 24.8 |
| Linoleic acid (18:2) | 12.2 | 0 |
| Linolenic acid (18:3) | 2.2 | 0 |

Conversion of Stearic Acid into Stearyl Alcohol

Stearic acid was converted into stearyl alcohol using a fixed-bed reactor containing a CuCr/$Al_2O_3$ catalyst. Specifically, 6 g of a commercially available CuCr/$Al_2O_3$ catalyst was placed in a fixed-bed reactor, the top and bottom of the catalyst were closed with glass wool, the remaining portion of the reactor was filled with silica beads, and a thermocouple was disposed so as to be in contact with the catalyst. The reaction temperature was increased to about 400° C. at a rate of about 5° C./min under conditions of $N_2$ flow rate of about 200 sccm and $H_2$ flow rate of 200 sccm, and was then maintained for about 3 hr at a reaction pressure of about 50 bar. Thereafter, the reaction temperature was decreased to about 300° C., after which the mixed solution of C18 fatty acid and ethanol at a molar ratio of 1:5 was fed at about 0.13 sccm, and the reactor was operated at a space velocity (WHSV) of about 1 $hr^{-1}$. Draining for the first 16 hr and then sampling at 8-hr intervals were performed, and hydrogenation activity and selectivity were measured. The reaction activity was measured at about 300° C., after which changes in the reaction activity were checked depending on changes in the reaction temperature and pressure. The stabilized product pattern results, observed two days after changes in the reaction conditions, were adopted, taking reaction stability into consideration. The conversion efficiency of the product was measured via SimDist analysis. The product selectivity and the presence or absence of side reactions were measured via GC-MS and SimDist analysis. The results are shown in Table 3 below.

TABLE 3

| | | CuCr/Al$_2$O$_3$ | | | |
|---|---|---|---|---|---|
| Sample ID | | 47 | 39 | 28 | 58 |
| Reaction conditions | Temp. (° C.) | 320 | 320 | 360 | 320 |
| | H$_2$ pressure (bar) | 50 | 40 | 40 | 40 |
| | H$_2$ flow rate (sccm) | 200 | 200 | 200 | 100 |
| Product pattern (%) | C17, C18 Paraffin | 0 | 0 | 0 | 0 |
| | C18 Alcohol | 83 | 79 | 46 | 67 |
| | C18 Acid | 4 | 13 | 21 | 11 |
| | C18 α-olefin | 0 | 0 | 0 | 4 |
| | C18 Acid-ethyl ester | 13 | 8 | 7 | 19 |
| | Others | 0 | 0 | 25 | 0 |

As is apparent from Table 3, the CuCr/Al$_2$O$_3$ catalyst exhibited high conversion efficiency of C18 fatty acid and high selectivity of C18 alcohol. The yield of C18 alcohol was 80% or more under conditions of a reaction temperature of about 320° C., H$_2$ pressure of 50 bar, and H$_2$ flow rate of 200 sccm. As such, side reactions did not occur. However, as the reaction temperature was increased (to 360° C. or higher), side reactions such as the formation of heavy hydrocarbons occurred, and the conversion efficiency was somewhat decreased. Furthermore, when the H$_2$ flow rate was lowered and thus the catalyst retention time of the reaction feed was increased, a small amount of C18 linear α-olefin was produced. However, this amount was very low, about 4%, thus making it possible to apply the above product industrially.

Evaluation of Dehydration Activity of Stearyl Alcohol

Stearyl alcohol was evaluated for dehydration activity in the presence of an alumina catalyst using a fixed-bed reactor. Specifically, 6 g of an alumina catalyst was placed in a fixed-bed reactor, the top and bottom of the catalyst were closed with glass wool, the remaining portion of the reactor was filled with silica beads, and a thermocouple was disposed so as to be in contact with the catalyst. The alumina had a surface area of about 260 m$^2$/g, an average pore size of about 10 nm, and a total pore volume of about 0.83 cc/g. The reactor was heated at a rate of 5° C./min under conditions of N$_2$ pressure of about 5 bar and N$_2$ flow rate of about 100 sccm, and was maintained at about 500° C. for 3 hr, whereby water was removed from the surface of the catalyst or the adsorbed gas was removed. Thereafter, the temperature was lowered to about 300° C., and a mixture comprising C18 fatty alcohol and n-heptane at a molar ratio of 6:4 was fed at 0.13 sccm, and the reactor was operated at a space velocity (WHSV) of about 1 hr$^{-1}$. Draining for the first 16 hr and then sampling at 8-hr intervals were performed, and the conversion activity of linear internal olefins and the selectivity thereof were measured. The C18 linear internal olefin was prepared at 400° C. and the properties thereof were measured. The stabilized product pattern results, observed two days after changes in the reaction conditions, were adopted, taking reaction stability into consideration. The conversion efficiency of the produced linear internal olefin was measured through SimDist analysis.

Based on the dehydration results, it was possible to convert the stearyl alcohol into C18 linear internal olefin at a high conversion efficiency of 95% or more. The remainder, comprising less than 5%, was determined to be an ester intermediate via GC-MS.

Figure 4:
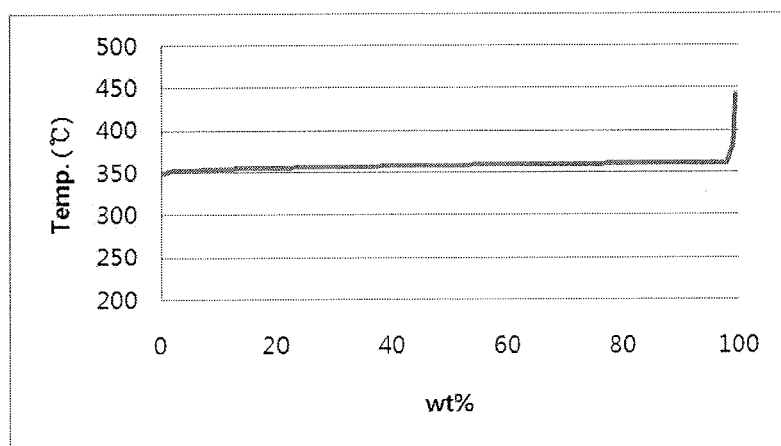
FIGS. 4 and 5 illustrate the results of SimDist analysis of the C18 linear internal olefin obtained from a stearyl alcohol feed in Example 1 using an r-$Al_2O_3$ catalyst.
Figure 5:
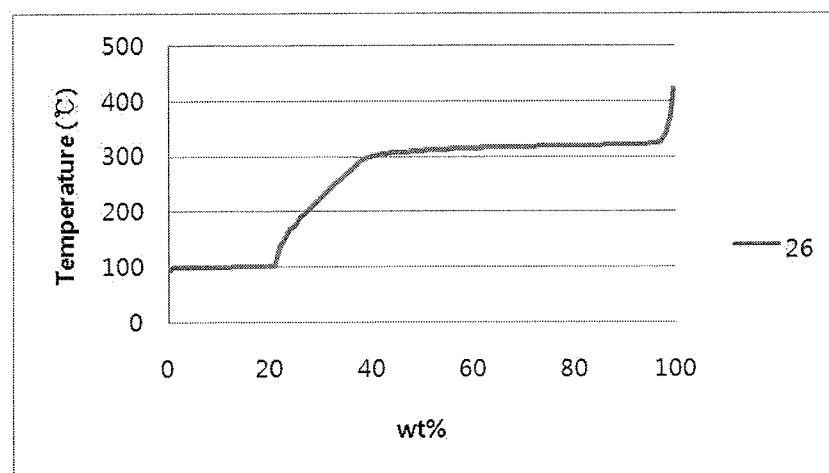

The results of SimDist analysis of the stearyl alcohol feed, obtained through the experiment, and the C18 linear internal olefin, obtained using the r-Al$_2$O$_3$ catalyst, are shown in FIGS. 4 and 5.

The purchased C18 linear α-olefin and the C18 linear internal olefin obtained in Example 1 were analyzed to determine the pour point and cloud point. The results are shown in Table 4 below.

TABLE 4

| | Pour point/Cloud point (° C./° C.) |
|---|---|
| C18 linear α-olefin | 18/20 |
| C18 linear internal olefin | −14/−13 |

Production of Estolide 100.3 g of the C18 linear internal olefin thus obtained and 82.2 g of palmitic acid were placed in a 500 cc flask, after which a stirring rod, a thermometer, and a cooling trap were connected thereto, and the mixture was stirred at 800 rpm and then heated to 210° C. When the reaction temperature reached 210° C., 9.2 g of sulfuric acid was added in droplets to the reaction system of the reactor. The sulfuric acid used was purchased from Across, and had a purity of 96% (in water). 3 hr after the addition of H$_2$SO$_4$, the operation was terminated and the reaction product was allowed to stand until it reached room temperature.

After termination of the reaction, the product was filtered, and unreacted palmitic acid was separated. The amount of the separated palmitic acid was 60.7 g. 119.8 g of the remaining solution was placed in a 4 L reactor, and a mixture comprising 963 g of methanol and 27.5 g of sulfuric acid was added. The above sulfuric acid product, made by Across, was used, and methanol made by SamChun Chemical, having a purity of 99.8%, was used. Thereafter, the temperature of the reactor was raised to 75° C. and maintained for 3 hr. Thereafter, the reaction was terminated, and the reaction product was allowed to stand until it reached room temperature.

In order to obtain a final product, the product was recovered, and the acidity thereof was checked using a mixed aqueous solution of KOH/ethanol (KOH/EtOH/DI water=0.1 g/30 g/1975 g). The mixed solution having no remaining acid was placed in a separatory funnel and allowed to stand. When the organic layer and the water layer containing salt and alcohol were separated in the separatory funnel, the water layer was removed, and the organic layer was isolated, from which the remaining salt and acid were then removed using 2 L of DI water. The amount of the organic layer was 120.5 g.

The yield of the product was measured through SimDist analysis of the organic layer. The results are shown in Table 5 below.

TABLE 5

| Product | Wt % |
|---|---|
| C18:1 Linear internal olefin | 42 |
| C16:0 Palmitic acid | 34 |
| Estolide (ester) | 21 |
| Estolide (acid) | 3 |

The obtained organic layer was further treated using a fractional distillation unit (Spaltrohr HMS 300 C; Fischer technology), and was cut on the basis of the boiling point, thereby separating the final product in estolide ester form. The amount of the finally obtained estolide ester material was 34.8 g.

Analysis of Properties of Estolide

In order to evaluate the applicability of the estolide produced in Example 1 as a lubricating oil, the properties thereof were analyzed for PP, viscosity (40° C., 100° C.), and iodine value, from which viscosity index (VI) was then calculated. The analyzed and calculated properties of estolide as lubricating oil are shown in Table 6 below.

TABLE 6

| Estolide | Viscosity at 40° C. (Cst) | Viscosity at 100° C. (Cst) | VI | Pour point (° C.) | Iodine value (cg/g) |
|---|---|---|---|---|---|
| Example 1 | 22.25 | 4.93 | 153.2 | −23 | 0.01 |

The estolide produced through the experiment exhibited very high VI, and had almost none of the remaining unsaturated double bonds. The pour point thereof was about −23° C., which made it suitable for use as lubricating oil. However, such estolide has very high VI compared to typical Group III base oil, and is thus regarded as good lubricating base oil.

EXAMPLE 2

Conversion of Fatty Acid Into Estolide 450.9 g of PFAD was placed in a 2 L reactor, stirred at 800 rpm, and heated to 210° C. When the reaction temperature reached 210° C., 22.5 g of sulfuric acid was added in droplets to the reaction system of the reactor. 3 hr after the addition of sulfuric acid, the operation was terminated. When the reaction temperature reached 70° C., the reaction product was placed in a 1 L glass bottle.

The product was cut on the basis of 400° C. using a fractional distillation unit (Spaltrohr HMS 300 C; Fischer technology), so that the estolide product was separated from the unreacted material and sulfuric acid.

The amount of the unreacted material, which was separated through fractional distillation from the product, was 186.1 g, and the amount of the product recovered as a material having a boiling point of 400° C. or higher was 250.4 g.

250.4 g of the recovered product was subjected to hydrodeoxygenation, yielding a final estolide product. The NiMo/ZrO$_2$ catalyst of Example 1 was loaded and pretreated in the same manner as in Example 1, followed by hydrodeoxygenation. The reaction conditions were the same as in Example 1, with the exception that the reaction temperature was set to 280° C. 8-hr sampling was performed, and the obtained product was recovered, and cut on the basis of 490° C. using a fractional distillation unit (Spaltrohr HMS 300 C; Fischer technology), thereby separating a final product having no carboxyl functional group from the unreacted estolide feed.

The amount of the final product obtained through fractional distillation was 135.8 g, and the amount of the unreacted estolide feed recovered as the material having a boiling point of 490° C. or higher was 62.1 g.

Based on the results of SimDist analysis, the final product was composed of a total of five components, wherein the amount of the material having a boiling point of 450° C. or less, regarded as the dimer of C16 and C18 fatty acids, was 68 wt % (21% and 47%), and the amount of the material having a boiling point of 450° C. or more, regarded as the trimer or higher, was 32 wt % (16%, 4%, 5%, remainder of 7%).

Analysis of Properties of Estolide

In order to evaluate the applicability of the estolide produced in Example 2 as a lubricating oil, the properties thereof were analyzed for PP, viscosity (40° C., 100° C.), and iodine value, from which the VI was then calculated. The analyzed and calculated properties of the estolide as lubricating oil are shown in Table 7 below.

TABLE 7

| Estolide | Viscosity at 40° C. (Cst) | Viscosity at 100° C. (Cst) | VI | Pour point (° C.) | Iodine value (cg/g) |
|---|---|---|---|---|---|
| Example 2 | 31.79 | 5.85 | 129.1 | −29 | 0.01 |

The estolide produced in Example 2 had improved pour point compared to the estolide product of Example 1, but the viscosity index thereof was significantly decreased. As for the properties as lubricating oil, the estolide of Example 2 exhibits higher VI and pour point than those of typical Group III base oil, and is thus regarded as good lubricating base oil.

The reason why the product is different from that produced in Example 1 is that the viscosity at 100° C. is greatly increased to 5.85, and thus the mixture of trimers or higher is produced, and C18:2 and C18:3 may participate in the estolide reaction, so that the estolide reaction is carried out not at the center position but at the unsaturated double bond adjacent to the center position, thus reducing the structure regularity. For this reason, the viscosity at 100° C. was further increased, and the viscosity index was remarkably decreased. Due to the effect of the material comprising trimers or higher, the pour point is considered to be much lower.

Although the embodiments of the present invention have been disclosed for illustrative purposes, those skilled in the art will appreciate that the present invention may be embodied in other specific ways without changing the technical spirit or essential features thereof. Therefore, the embodiments disclosed in the present invention are not restrictive but are illustrative.

The invention claimed is:

1. A method of producing an estolide having high structural stability, comprising:
    a) preparing a fatty acid mixture comprising C4 to C24 from biomass-derived oil;
    b) separating the fatty acid mixture into a C16 fatty acid and a C18 fatty acid, respectively;
    c) converting the separated C18 fatty acid into a C18 or C17 linear internal olefin; and
    d) subjecting the C18 or C17 linear internal olefin and the separated C16 fatty acid to an estolide reaction, wherein the estolide reaction is a crosslinking reaction of unsaturated double bonds of hydrocarbons with a fatty acid using an acid catalyst, thus obtaining an estolide.

2. A method of producing an estolide having high structural stability, comprising:
    A) preparing a fatty acid mixture comprising C4 to C24 from biomass-derived oil; and B) subjecting the fatty acid mixture to an estolide reaction and then hydrodeoxygenation, wherein the estolide reaction is a crosslinking reaction of unsaturated double bonds of hydrocarbons with a fatty acid using an acid catalyst, thus obtaining an estolide.

3. The method of claim 1, wherein c) comprises converting the C18 fatty acid into a C18 linear internal olefin through partial hydrogenation and dehydration.

4. The method of claim 1, wherein c) comprises converting the C18 fatty acid into a C17 linear internal olefin through decarbonylation.

5. The method of claim 1, further comprising e) performing hydrotreating to increase stearic acid content, between steps a) and b).

6. The method of claim 1, further comprising f) hydrotreating the C18 fatty acid separated in b) to increase stearic acid content, between steps b) and c).

7. The method of claim 2, further comprising C) performing hydrotreating to increase stearic acid content, after A).

8. The method of claim 2, further comprising D) separating or purifying the estolide obtained in B) to obtain a desired estolide.

9. The method of claim 1, wherein a) or A) is performed through de-esterification or hydrolysis of triglyceride in the biomass-derived oil.

10. The method of claim 2, wherein a) or A) is performed through de-esterification or hydrolysis of triglyceride in the biomass-derived oil.

11. An estolide, produced by the method of claim 1, wherein the estolide comprises an estolide represented by Chemical Formula 1 or Chemical Formula 2 below:

[Chemical Formula 1]

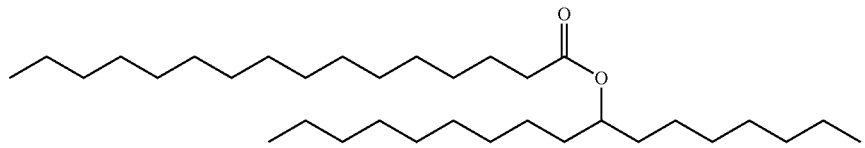

[Chemical Formula 2]

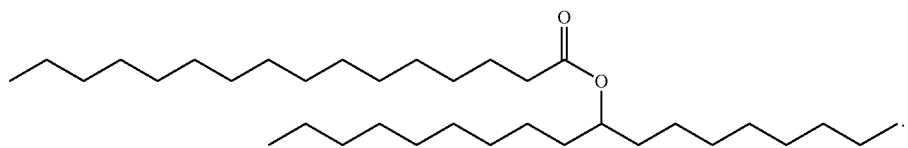

12. An estolide, produced by the method of claim 2, wherein the estolide comprises an estolide represented by Chemical Formula 1 or Chemical Formula 2 below:

[Chemical Formula 1]

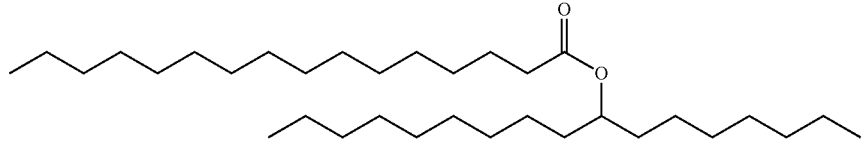

[Chemical Formula 2]

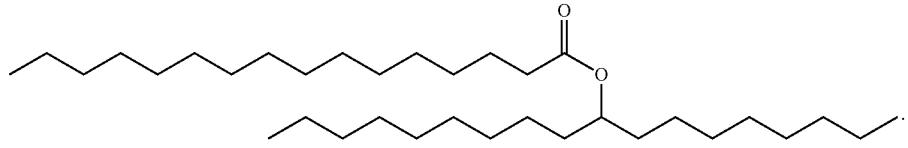

13. A lubricating oil, comprising an estolide produced by the method of claim 1, wherein the estolide comprises an estolide represented by Chemical Formula 1 or Chemical Formula 2 below:

[Chemical Formula 1]

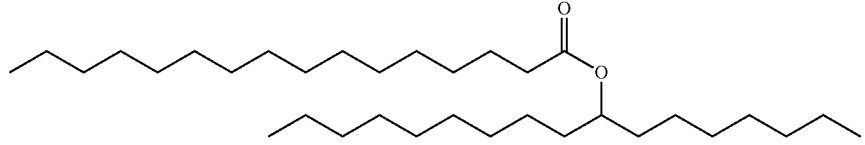

-continued
[Chemical Formula 2]
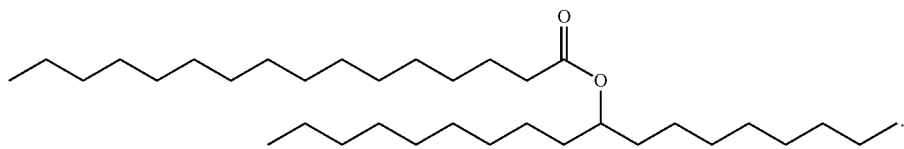
14. A lubricating oil, comprising an estolide produced by the method of claim 2, wherein the estolide comprises an estolide represented by Chemical Formula 1 or Chemical Formula 2 below:
[Chemical Formula 1]
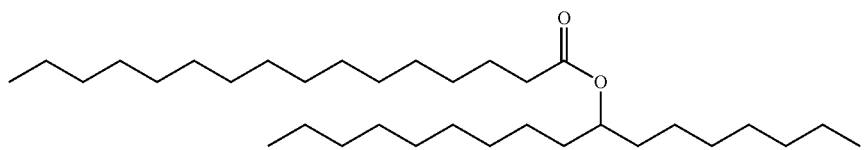
[Chemical Formula 2]
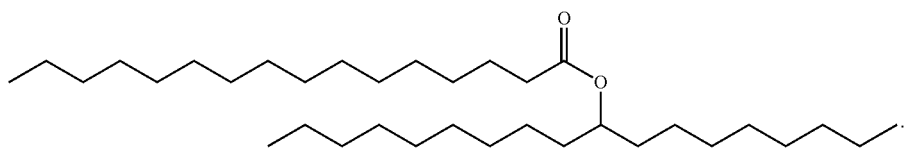
* * * * *

UNITED STATES PATENT AND TRADEMARK OFFICE
CERTIFICATE OF CORRECTION

| | | |
|---|---|---|
| PATENT NO. | : 9,845,280 B2 | Page 1 of 1 |
| APPLICATION NO. | : 14/884247 | |
| DATED | : December 19, 2017 | |
| INVENTOR(S) | : Hee Jung Jeon, Jong Su Lee and Yong Woo Kim | |

It is certified that error appears in the above-identified patent and that said Letters Patent is hereby corrected as shown below:

On the Title Page

Under (71) Applicant:
Please replace the second applicant name from "SK LUBRICANTS CO., LTD., Seoul (KR)" to "SK ENMOVE CO., LTD., Seoul (KR)"; and Under (73) Assignee:
Please replace the second assignee name from "SK LUBRICANTS CO., LTD., Seoul (KR)" to "SK ENMOVE CO., LTD., Seoul (KR)".

Signed and Sealed this
Thirteenth Day of August, 2024

Katherine Kelly Vidal
*Director of the United States Patent and Trademark Office*